US009880092B2

(12) United States Patent
Foy et al.

(10) Patent No.: US 9,880,092 B2
(45) Date of Patent: Jan. 30, 2018

(54) VISUAL INDICATION TEST KIT

(71) Applicant: Morphix Technologies, Inc., Virginia Beach, VA (US)

(72) Inventors: Deborah Foy, Chesapeake, VA (US); Edward Locke, Norfolk, VA (US); Julian Parker, Chesapeake, VA (US); Anthony Pomozzi, Chesapeake, VA (US); Matthew Rixon, III, Virginia Beach, VA (US)

(73) Assignee: Morphix Technologies, Inc., Virginia Beach, VA (US)

( * ) Notice: Subject to any disclaimer, the term of this patent is extended or adjusted under 35 U.S.C. 154(b) by 186 days.

(21) Appl. No.: 14/451,893

(22) Filed: Aug. 5, 2014

(65) Prior Publication Data
US 2015/0044777 A1 Feb. 12, 2015

Related U.S. Application Data

(60) Provisional application No. 61/862,677, filed on Aug. 6, 2013.

(51) Int. Cl.
*G01N 21/29* (2006.01)
*B01L 3/00* (2006.01)
(Continued)

(52) U.S. Cl.
CPC .......... *G01N 21/293* (2013.01); *B01L 3/5029* (2013.01); *B01L 2200/16* (2013.01);
(Continued)

(58) Field of Classification Search
CPC ............... G01N 2800/52; G01N 21/76; G01N 21/0303; G01N 21/05; G01N 21/78;
(Continued)

(56) References Cited

U.S. PATENT DOCUMENTS

| 5,648,047 A | 7/1997 | Kardish et al. |
| 6,613,576 B1 | 9/2003 | Rodacy et al. |

(Continued)

FOREIGN PATENT DOCUMENTS

| CN | 1843315 A | * | 10/2006 | |
| CN | 203094782 U | * | 7/2013 | |
| GB | 551027 A | * | 2/1943 | ............... B67B 7/92 |

OTHER PUBLICATIONS

ISR/WO for PCT/US2014/049744 file Aug. 5, 2014 dated Apr. 16, 2015, 11 pages.

*Primary Examiner* — Yelena G Gakh
(74) *Attorney, Agent, or Firm* — Armstrong Teasdale LLP (57) ABSTRACT

A test kit is provided. The test kit includes a case including a top including a plurality of indicator pads and a crushing plate rotatable between a first position and a second position, the crushing plate including a plurality of crushing ribs. The case further includes a bottom hingedly coupled to the top, the bottom including a plurality of reagent ampoules storing reagents. When the case is closed with the crushing plate in the second position, the plurality of crushing ribs crush the the plurality of reagent ampoules. The test kit further includes a collector including a collector body, a plurality of swabs extending through the collector body, a removable cover covering a first side of the collector body, and a collector handle coupled to the collector body, wherein the collector is nestable within the case.

16 Claims, 10 Drawing Sheets

(51) Int. Cl.
G01N 1/02 (2006.01)
G01N 31/22 (2006.01)

(52) U.S. Cl.
CPC .............. *B01L 2300/0663* (2013.01); *B01L 2300/0672* (2013.01); *B01L 2300/0816* (2013.01); *B01L 2300/0867* (2013.01); *B01L 2400/0406* (2013.01); *B01L 2400/0683* (2013.01); *G01N 31/228* (2013.01); *G01N 2001/024* (2013.01)

(58) Field of Classification Search
CPC ............ G01N 21/8483; A61K 2300/00; B01L 2300/0816; B01L 3/5029; B01L 2300/0867; B01L 2200/10; B01L 2400/0688; B01L 3/5027; B01L 3/05
See application file for complete search history.

(56) References Cited

U.S. PATENT DOCUMENTS

| | | | |
|---|---|---|---|
| 7,749,440 B1 | 7/2010 | Genovese | |
| 7,939,029 B2 | 5/2011 | Eckels et al. | |
| 8,252,602 B2 | 8/2012 | Haas | |
| 8,293,107 B1* | 10/2012 | Lobovsky | B01D 17/0202 210/321.79 |
| 2003/0157588 A1 | 8/2003 | Matner et al. | |
| 2008/0254550 A1 | 10/2008 | Nathaniel | |
| 2010/0323343 A1 | 12/2010 | Egan et al. | |
| 2011/0200999 A1* | 8/2011 | Soni | C12Q 1/689 435/6.11 |

\* cited by examiner

VISUAL INDICATION TEST KIT

CROSS REFERENCE TO RELATED APPLICATIONS

This application claims the priority of Provisional Patent Application Ser. No. 61/862,677, filed Aug. 6, 2013, which is hereby incorporated by reference in its entirety.

GOVERNMENT INTEREST

Development of the present invention was supported in part by the U.S. Department of Defense under grant number H92222-12-C-0009. The government may have certain rights in the invention.

BACKGROUND

The embodiments described herein relate generally to visual indication tests for the presence of substances, and, more particularly, to systems and methods for performing multiple visual indication tests using a single extraction of analytes from a substrate.

Visual indication can occur by a multitude of techniques, including, among others, colorimetric, fluorescence or chemiluminescence. For some of these techniques, excitation other than ambient light may be required for the human eye to see the visual indication. At least some known devices that use visual indication technology to detect substances on or in a substrate typically require a multitude of individual cycles of analyte extraction and visual indication testing. In an alternative approach, at least some known devices require a single extraction followed by a serial test sequence that requires the user to observe the result of each step, and then take the appropriate action based on the result of the previous step.

BRIEF DESCRIPTION OF THE DISCLOSURE

In one aspect, a visual indication test kit is provided. The visual indication test kit includes a single collector including a plurality of plugs, wherein the plurality of plugs are configured to serve as extraction points for analytes, and mix a plurality of reagents with a plurality of analytes extracted onto the plurality of plugs, wherein the mixing of the plurality of reagents and the plurality of analytes facilitates performing a plurality of visual indications.

In another aspect, a method for performing a plurality of visual indication tests using a visual indication test kit that includes a collector is provided. The method includes extracting analytes using a plurality of plugs disposed on the collector, mixing a plurality of reagents with the analytes extracted onto the plurality of plugs, and performing a plurality of visual indications using the analyte and reagent mixtures.

BRIEF DESCRIPTION OF THE DRAWINGS

FIGS. 1-15 show example embodiments of systems and methods for performing visual indication tests as described herein.

DETAILED DESCRIPTION OF THE DISCLOSURE

The embodiments described herein provide a visual indication test kit capable of running multiple visual indication tests from a single extraction of analytes from a substrate. The visual indication test kit includes multiple flow paths that allow specific visual indication reagents to reach specific analytes, resulting in a visual indication response if the analyte is present. In some embodiments, more than one reagent may flow to reach a specific analyte. In such embodiments, the timing of the reagent flow may be important, and may be controlled using hydrophobic and/or hydrophilic materials.

The following detailed description illustrates the disclosure by way of example and not by way of limitation. The description clearly enables one skilled in the art to make and use an example visual indication test kit, and describes several embodiments, adaptations, variations, alternatives, and uses of a visual indication test kit, including what is presently believed to be the best mode of carrying out the disclosure.

Figure 1:
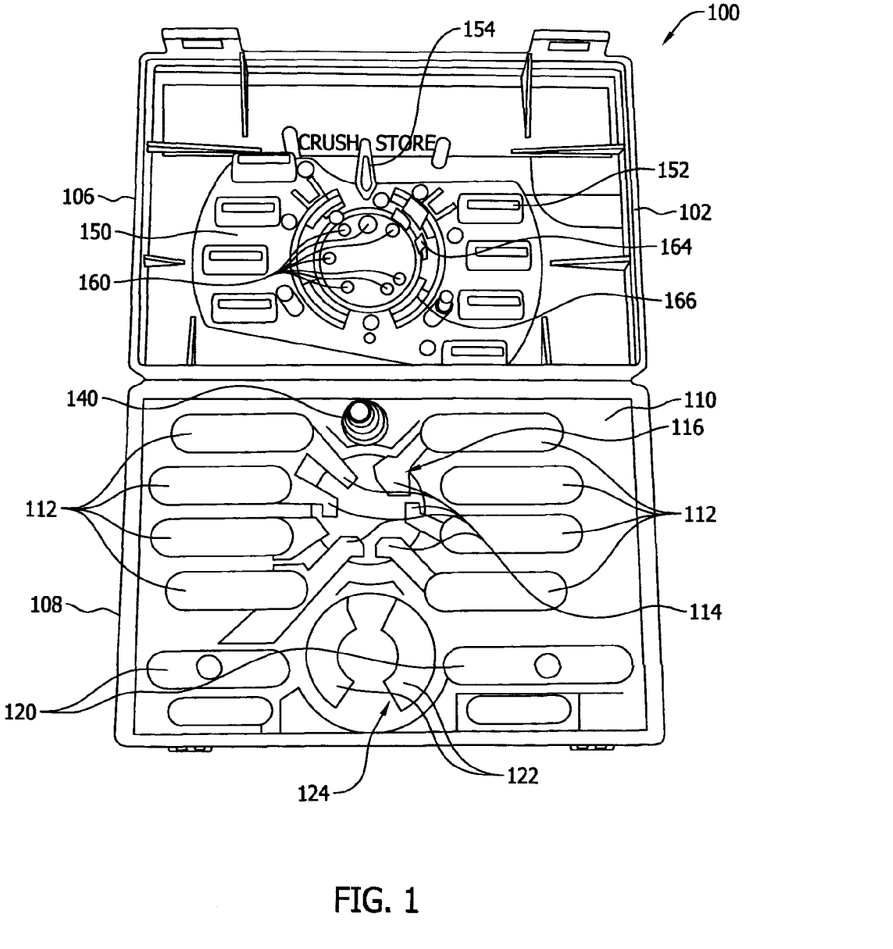
FIG. 1 is a perspective view of a case for a visual indication test kit.
Figure 2:
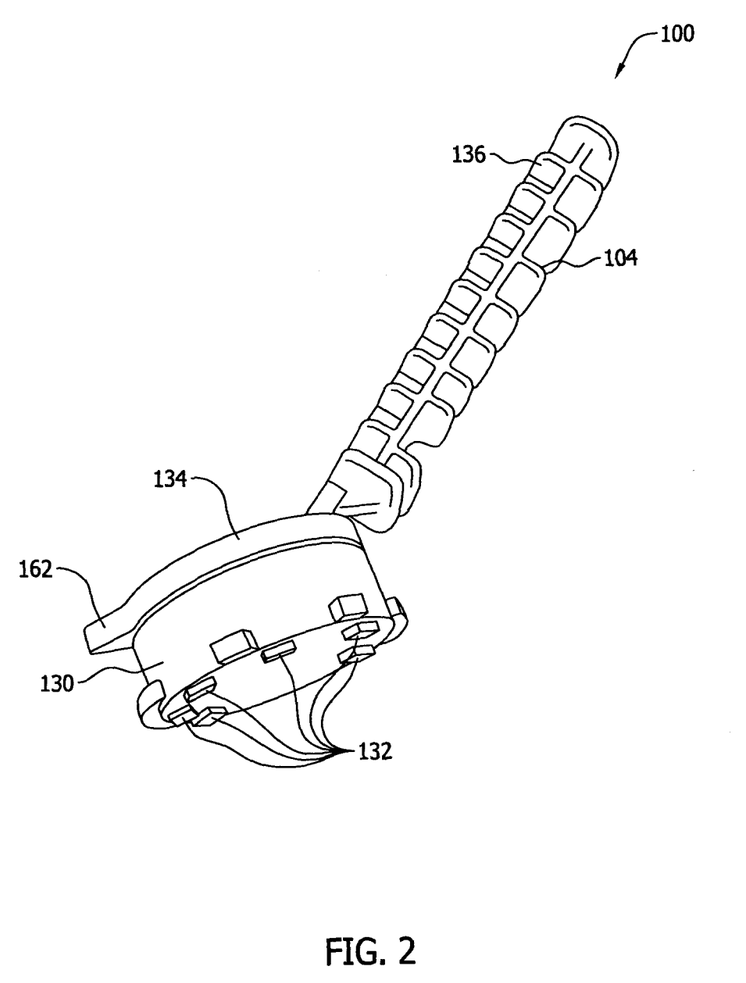
FIG. 2 is a perspective view of a collector for a visual indication test kit.

Referring now to the drawings, FIG. 1 is a perspective view of an example case 102 for a visual indication test kit 100, and FIG. 2 is a perspective view of an example collector 104 for the visual indication test kit 100. For transporting and packaging purposes, the 104 collector nests within the case 102 (see FIGS. 4 and 5), such that all of the elements of the visual indication test kit 100 are packaged together.

The case 102 includes a top 106 hingedly coupled to a bottom 108. The case bottom 108 includes a blister pack 110 that encloses a plurality of ampoules 112 each storing a predetermined reagent. In the example embodiment, the blister pack 110 includes a thin film top and a thin film bottom that form a sealed container for the ampoules 112. Alternatively, the blister pack 110 includes the thin film top, but does not include the thin film bottom. In such embodiments, this film top attaches to the case bottom 108.

In the example embodiment, the case bottom 108 includes eight reagent ampoules 112. Alternatively, the case bottom 108 may include any number of reagent ampoules 112 that enables visual indication kit 100 to function as described herein. When the reagent ampoules 112 are crushed, the reagents flow to corresponding reagent wicks 114. The timing of the reagent flow through the reagent wicks 114 may be controlled based on a porosity, flow path, capacity, material of construction, hydrophobicity, and/or hydrophilicity of each reagent wick 114. A hole 116 is defined in the blister pack 110 such that the reagent wicks 114 are exposed. The reagent wicks 114 deliver the reagents to the collector 104 for visual indications, as described herein. In some embodiments, one reagent wick 114 receives reagents from two or more different reagent ampoules 112.

The blister pack 110 also includes at least one ampoule 120 storing a wetting agent. Different wetting agents or the same wetting agent may be stored in different ampoules 120. In the example embodiment, the case bottom 108 includes two wetting agent ampoules 120. Alternatively, the case bottom 108 may include any number of wetting agent ampoules 120 that enables visual indication kit 100 to function as described herein. When the wetting agent ampoules 120 are crushed, the wetting agents flow to corresponding wetting wicks 122. A hole 124 is defined in the blister pack 110 such that the wetting wicks 122 are exposed. The wetting wicks 122 deliver the wetting agents to the collector 104 to facilitate extracting analytes, as described herein.

As shown in FIG. 2, in the example embodiment, the collector 104 includes a collector body 130 that includes a plurality of plugs 132, or swabs. The plugs 132 extend through the collector body 130 and function as wicks to guide the flow of the reagents through the collector 104, as described herein. A collector cover 134 facilitates preventing a user from contaminating the plugs 132 while collecting the analyte. A collector handle 136 is pivotably coupled to the collector body 130.

As noted above, the collector 104 is initially nested within the case 102. Specifically, the collector body 130 seats atop the wetting wicks 122, and the collector handle 136 extends above the reagent wicks 114 (see FIGS. 4 and 5). A lifting spring 140 biases the collector handle 136 upward (i.e., away from the case bottom 108), which aids the user in removing the collector 104 from the case 102.

The case top 106 includes a rotatable crushing plate 150 including a plurality of crushing ribs 152. The crushing plate 150 is rotatable between a first position (shown in FIGS. 1 and 8) and a second position (shown in FIG. 9). When closing the case 102 with the crushing plate 150 in the first position, the crushing ribs 152 fit between the reagent ampoules 112 in the blister pack 110. When closing the case 102 with the crushing plate 150 in the second position, the crushing ribs 152 contact the blister pack 110 and crush the reagent ampoules 112, releasing the reagents stored therein. The crushing plate 150 includes an alignment pointer 154 that indicates whether the crushing plate 150 is in the first position or the second position.

The case top 106 further includes a plurality of indicator pads 160. As described herein, the reagent/analyte mixture contacts the indicator pads 160, providing various visual indications for the user. That is, the collector body 130 engages the case top 106 such that the plurality of plugs 132 are aligned with the plurality of indicator pads 160. Specifically, the collector body 130 is inserted into the case top 106 such that an alignment pointer 162 on the collector cover 134 is aligned with the alignment pointer 154 on the crushing plate 150. The collector body 130 engages the case top 106 using one or more snap-fit mechanisms 164. Further, one or more slotted mechanisms 166 further facilitate securing the collector body 130 to the case top 106 when the crushing plate 150 is rotated from the first position to the second position.

Figure 3:
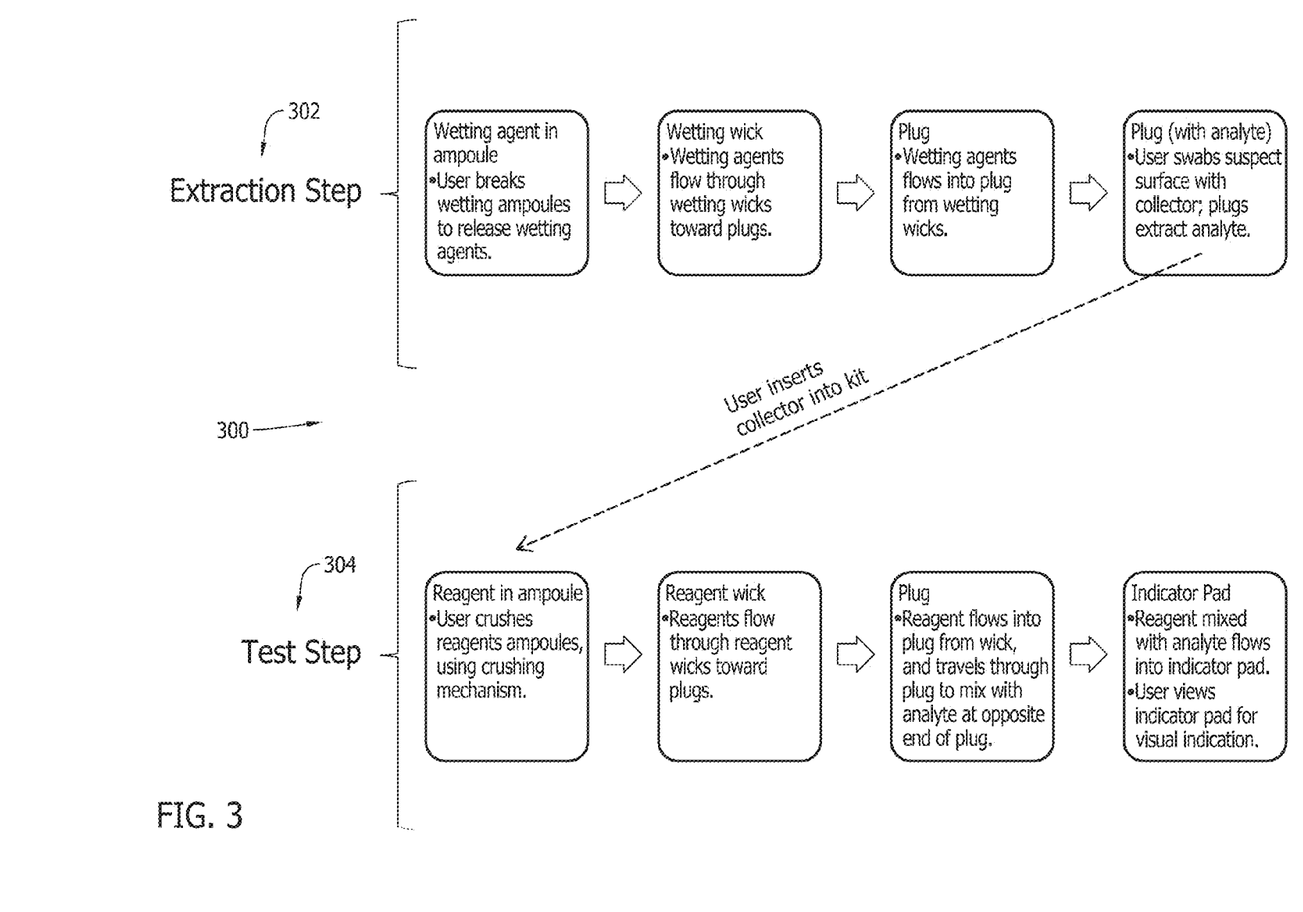
FIG. 3 is a flow diagram of an example method for performing visual indication tests using the kit shown in FIGS. 1 and 2.

FIG. 3 is a flow diagram of an example method 300 for performing visual indication tests using the kit 100 shown in FIGS. 1 and 2. After opening the case 102, as part of an extraction step 302, the user breaks the wetting agent ampoules 120 to release the wetting agents stored therein. At this point, the collector body 130 is positioned atop the wetting wicks 122. The released wetting agents flow into the wetting wicks 122 toward the plugs 132, and subsequently flow into the plugs 132 from the wetting wicks 122.

In the example embodiment, not all plugs 132 are wetted with wetting agents. The plugs 132 function as swabs to extract a substance from a surface in the example embodiment. However, a first swab for one analyte may have improved collection efficiency if wetted with water, a second swab for a second analyte may have improved collection efficiency if wetted with an organic solvent or some other extraction chemical, and a third swab for a third analyte may have improved collection efficiency if dry. Accordingly, to facilitate maximizing collection efficiency, it may be desirable, for example, to wet at least one plug 132 with water, wet at least one plug 132 with an organic solvent or some other extraction chemical, and keep at least one plug 132 dry. The combination of differently prepared plugs in the same collector 104 eliminates the need to conduct repeated sampling with individual swabs. In some embodiments, all of the plugs 132 are wetted. In other embodiments, none of the plugs 132 are wetted.

Accordingly, the example embodiment utilizes plugs 132 as swabs to extract a substance. Alternatively, one or more chemicals may be used to extract a substance from a substrate. In one approach, the substrate is covered with an extraction chemical that releases the substance from the substrate into the extraction chemical. In an alternative approach, the extraction chemical is mixed with the substrate to release the substance from the substrate into the extraction chemical.

The user removes the collector 104 (with at least some of the plugs 132 wetted), and swabs a suspect surface to collect analyte on the plugs 132. The collector 104 is then inserted into the case 102. More specifically, the collector body 130 is inserted into the case top 106 such that the plugs 132 contact the indicator pads 160.

To perform a test step 304, with the crushing plate 150 in the second position and the collector body 130 inserted in the case top 106, the user closes the case 102. When closing the case 102, the crushing ribs 152 crush the reagent ampoules 112, releasing the reagents stored therein. The reagents flow into the reagent wicks 114 toward the plugs 132, and subsequently flow into the plugs 132 from the reagent wicks 114. The reagents flow through the plugs 132 to mix with the analyte at an end of the plugs 132 that is opposite from an end of the plugs 132 that the reagents entered. That is, the reagents flow from an end of the plugs 132 proximate the reagent wicks 114 to an end of the plugs 132 proximate the indicator pads 160. As described above, in some embodiments, a single plug 132 may receive a plurality of reagents. In such embodiments, the timing of the reagents reaching the analyte may be critical to performing proper visual indications. Accordingly, the migration rate of each reagent through the plug 132 may be controlled, for example, based on a porosity, flow path, capacity, material of construction, hydrophobicity, and/or hydrophilicity of the plug 132. For example, a single plug 132 may include a hydrophobic portion for slowing down a migration rate of a first reagent through the plug 132, and a hydrophilic portion for speeding up a migration rate of a second reagent through the plug 132. Moreover, in some embodiments, a plug 132 may include other features and/or characteristics that facilitate mixing a plurality of reagents therein.

The reagents mix with the analyte at each plug 132, and the mixtures flow to corresponding indicator pads 160. Similar to the plugs 132 and the reagent wicks 114, the migration rate of reagents through an indicator pad 160 may be controlled, for example, based on a porosity, flow path, capacity, material of construction, hydrophobicity, and/or hydrophilicity of the indicator pad 160. Accordingly, the plugs 132, reagent wicks 114, and/or indicator pads 160 may include or constitute a flow control material.

By viewing the indicator pads 160, the user can observe visual indications that indicate the presence of one or more chemicals. The indicator pads 160 also play a role in filtering particulate debris, for example without limitation, dirt, dust, and/or sand, to allow extraction to take place in dirty environments with minimal impact to the test results. For example, an indicator pad 160 may change color in the presence of a predetermined chemical. In the example embodiment, the plurality of indicator pads 160 indicate the presence of nitroaromatics (e.g., TNT, DNT, and Tetryl), nitramines and nitrate esters (e.g., RDX, HMX, PETN, EGDN, and NG), inorganic nitrates (e.g., urea nitrate, ammonium nitrate, and black powder), chlorates and bromates (e.g., potassium chlorate and potassium bromate), peroxides (e.g., TATP and HMTD), acids (e.g., nitric acid, sulfuric acid, and citric acid), and bases (e.g., potassium hydroxide and sodium hydroxide). Alternatively, reagents and indicator pads 160 may facilitate indicating the presence of any substance that enables the visual indication test kit 100 to function as described herein. For example and without limitation, the visual indication could indicate the presence of narcotics, gunshot residue, forensic materials, chemical warfare agents, environmental contaminants, and/or biological warfare agents. In an alternate embodiment, the indication can be matched to a color chart to further identify the presence of or amount of an analyte.

FIGS. 4-13 are diagrams explaining a method for performing visual indication tests using the kit 100 shown in FIGS. 1 and 2.

Figure 4:
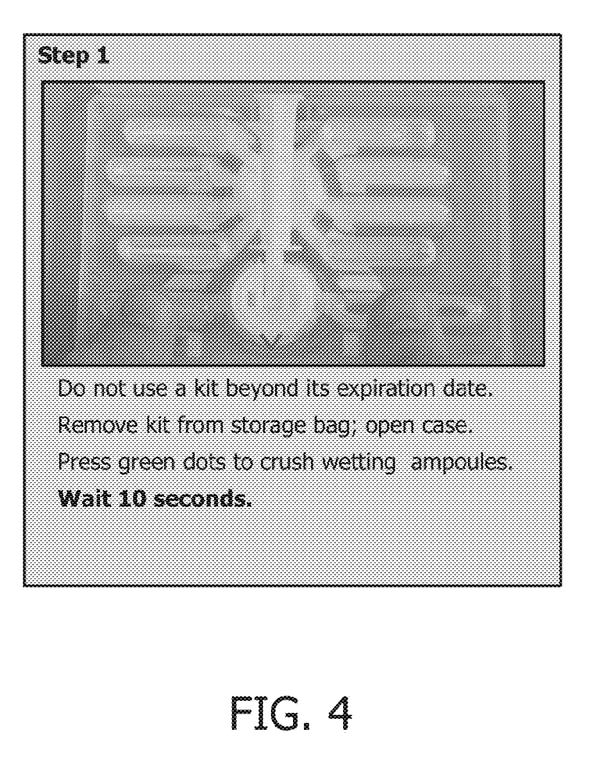
FIGS. 4-13 are diagrams explaining an example method for performing visual indication tests using the kit shown in FIGS. 1 and 2.

As shown in FIG. 4, when the user opens the case 102, the collector 104 is already nested inside the case 102. In the example embodiment, prior to use, the kit 100 is stored in a storage bag (not shown). To release the wetting agents, as shown in FIG. 4, the user presses green dots on the blister pack 110 to crush the wetting agent ampoules 120. In the example embodiment, the user waits approximately 10 seconds for the wetting agents to flow into the wetting wicks 122.

Figure 5:
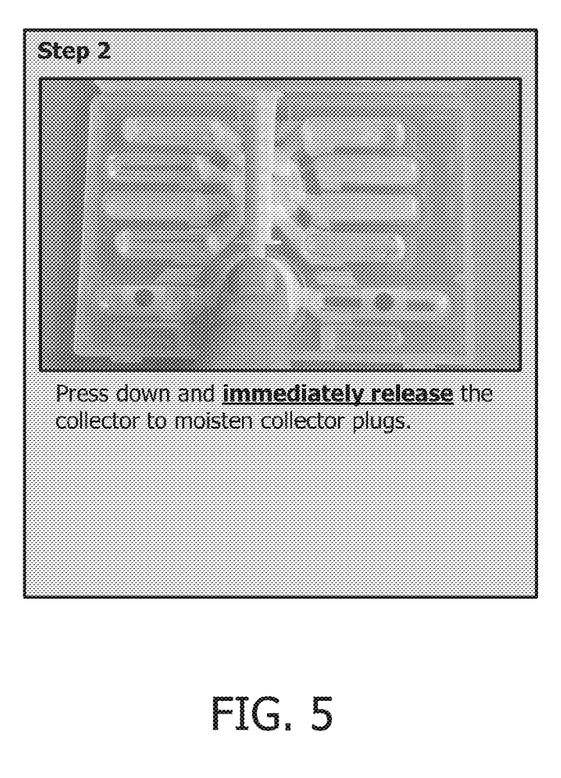

As shown in FIG. 5, to transfer the wetting agents from the wetting wicks 122 to at least some of the plugs 132, the user briefly presses down on the collector 104. This causes the plugs 132 to contact the wetting wicks 122, moistening the plugs 132.

Figure 6:
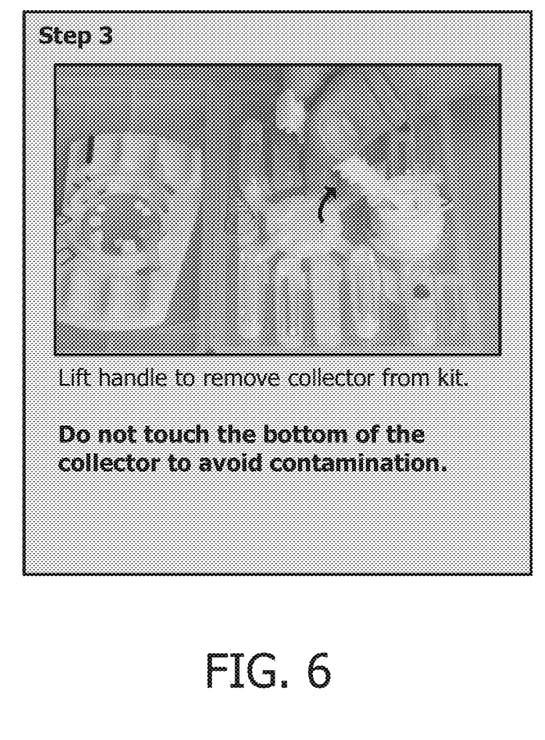

As shown in FIG. 6, the user lifts the collector handle 136 to remove the collector 104 from the case 102. The lifting spring 140 biases the collector handle 136 upward (i.e., away from the case bottom 108), aiding the user in removing the collector 104 from the case 102. To avoid contamination of the collector 104, the collector cover 134 keeps potential contaminants from coming in contact with the plugs 132 at the top of the collector 104, and at no point should the user touch the bottom of the collector 104 (i.e., the portion of the collector 104 with the plugs 132 exposed).

Figure 7:
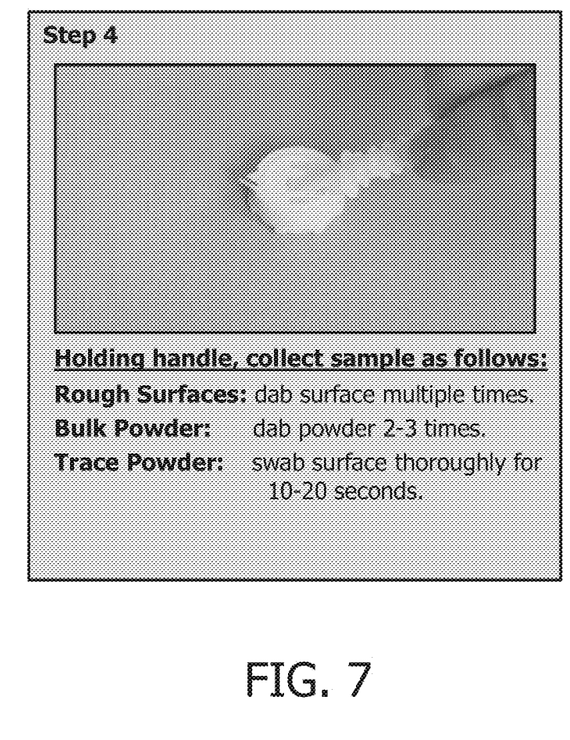

As shown in FIG. 7, the user swabs a surface of interest with the collector 104 to extract analytes from the surface. The collector 104 may be used to collect trace (i.e., relatively small) and/or bulk (i.e., relatively large, visible) amounts of material (e.g., a powder). For example, to collect trace amounts of material, the surface of interest is swabbed thoroughly for approximately 10-20 seconds. To collect bulk amounts of material, the material itself is dabbed multiple times. For a relatively rough surface of interest containing the material, the surface of interest is also dabbed multiple times. Alternatively, the surface of interest may be contacted with the collector 104 using any technique that enables the collector 104 to function as described herein.

Figure 8:
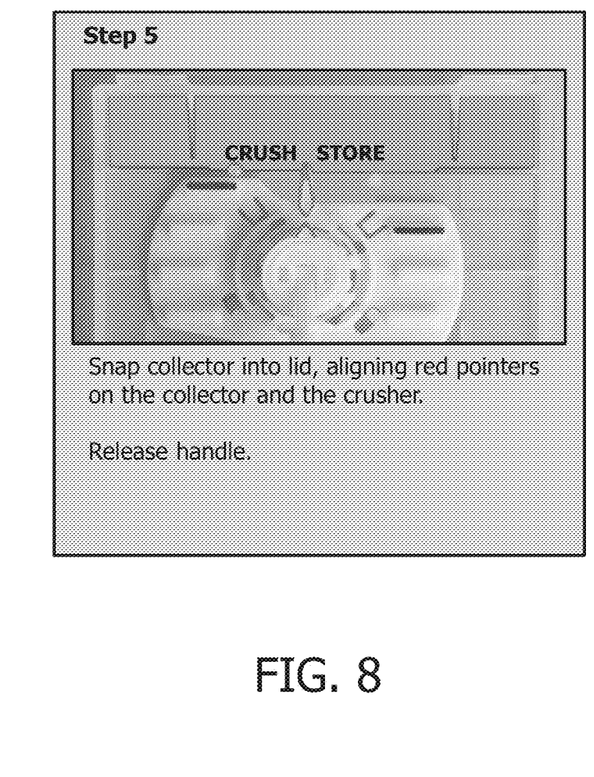

As shown in FIG. 8, the collector 104, and more specifically, the collector body 130, is snapped into the case top 106, or lid. To ensure alignment between the plurality of plugs 132 and the plurality of indicator pads 160, the alignment pointer 154 on the crushing plate 150 is aligned with the alignment pointer 162 on the collector cover 134. To facilitate alignment, the alignment pointers 154 and 162 may be a predetermined color (e.g., red).

Figure 9:
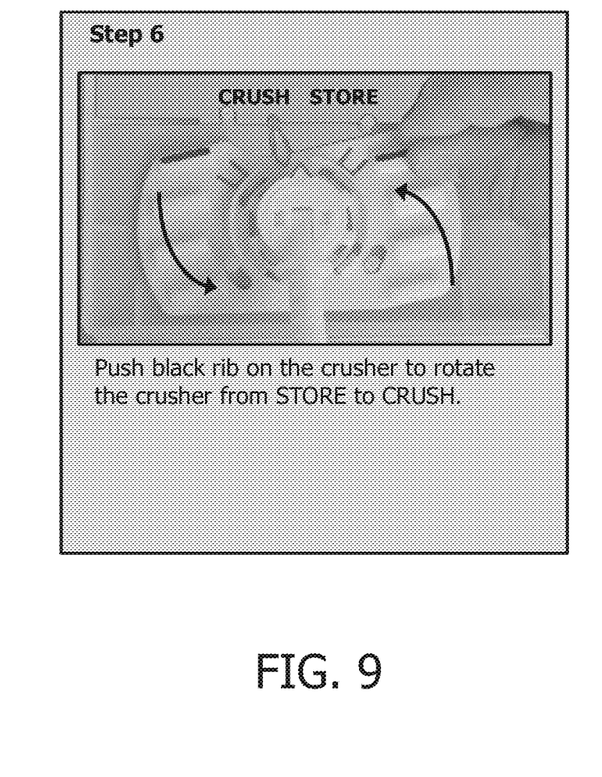

As shown in FIG. 9, once the collector 104 is snapped into the case top 106, the user rotates the crushing plate 150 by pushing on one of the crushing ribs 152. To facilitate aiding the user in rotating the crushing plate 150, at least some of the crushing ribs 152 may be a predetermined color (e.g., black). Further, in the example embodiment, rotating the crushing plate 150 from the first position to the second position causes the alignment pointer 154 on the crushing plate to point to "CRUSH" instead of "STORE".

Figure 10:
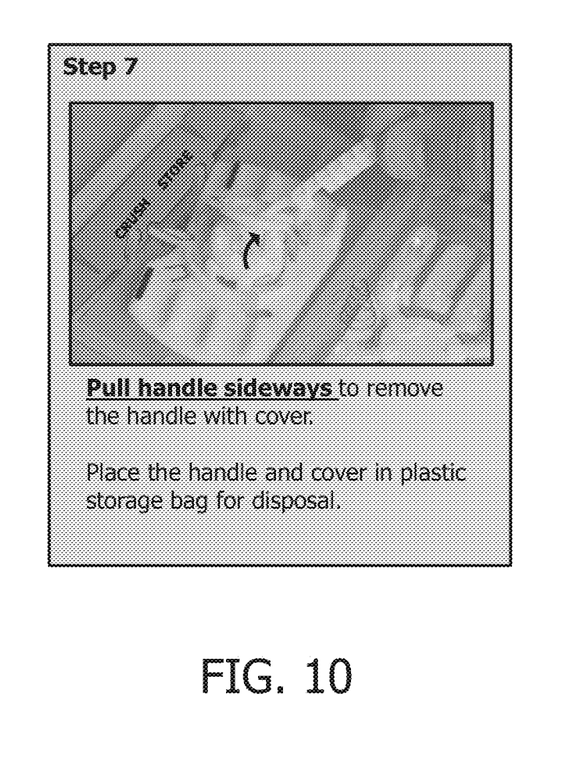

As shown in FIG. 10, the user pulls the collector handle 136 sideways to remove the collector handle 136 and the collector cover 134. Removing the collector cover 134 exposes the plugs 132 on the top of the collector body 130. The collector handle 136 and collector cover 134 may be placed in the storage bag for disposal.

Figure 11:
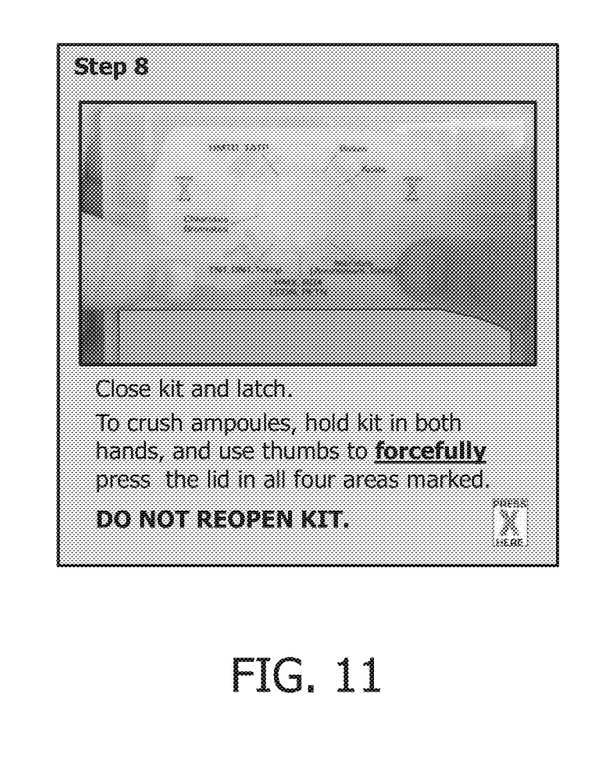

As shown in FIG. 11, the user closes the case 102. In the example embodiment, the case 102 includes at least one latch 170 for securing the case 102 in the closed position. As the crushing plate 150 is in the second position when the case 102 is closed, the crushing ribs 152 are in a position to crush the reagent ampoules 112 in the case bottom 108, releasing the reagents. In the example embodiment, the case top 106 includes four indicators (e.g., a blue "X") that indicate where the user should apply pressure to ensure the reagent ampoules 112 are completely crushed. Alternatively, the case top 106 may include any number of indicators that enable the case 102 to function as described herein. The reagents flow into the reagent wicks 114, and subsequently, into the exposed plugs 132.

Figure 12:
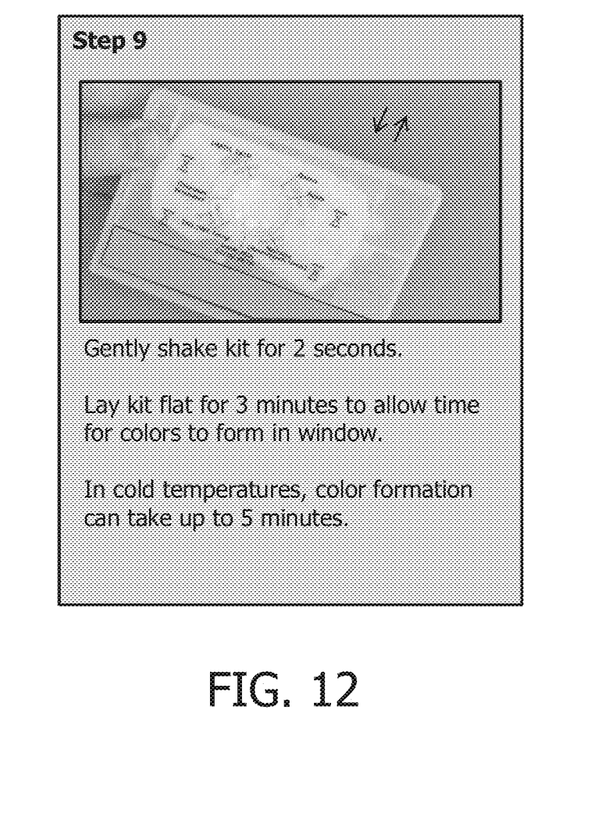

As shown in FIG. 12, to ensure the reagents flow through the plugs 132 and mix with the analytes, the user gently shakes the closed case 102 for a few seconds. The reagent/analyte mixtures from each plug 132 flow to the corresponding indicator pads 160. A user may lay the kit flat (e.g., for 3 minutes) to allow time for colors to form in the indicator pads 160.

Figure 13:
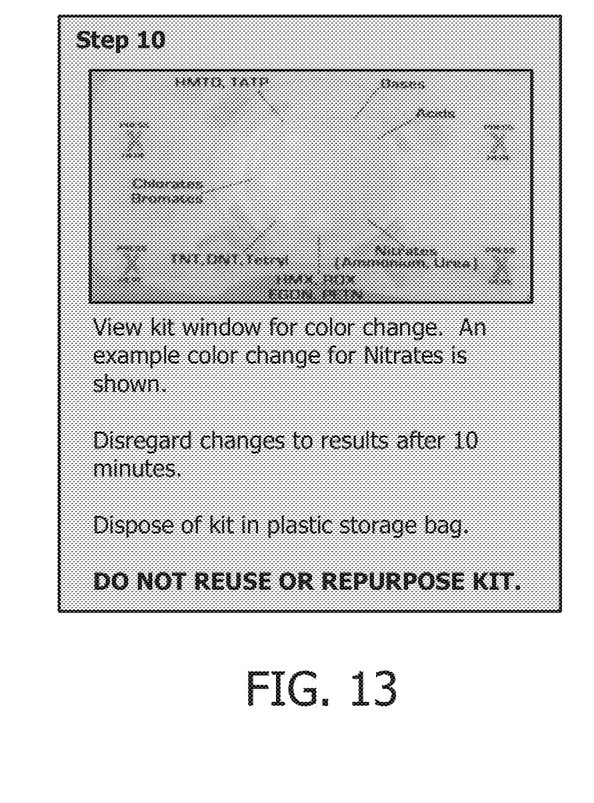

As shown in FIG. 13, the user views the plurality of indicator pads 160 to determine whether predetermined chemicals are present. To facilitate viewing the plurality of indicator pads 160, at least a portion of the case top 106 is substantially transparent. Further, in the example embodiment, the case top 106 includes labels, or indicia (e.g., "Bases", "Acids", "Nitrates", etc.) that identify which indicator pads 160 indicate the presence of which chemicals. Once the user has viewed the plurality of indicator pads 160, the kit 100 may be placed in the storage bag for disposal.

Figure 14:
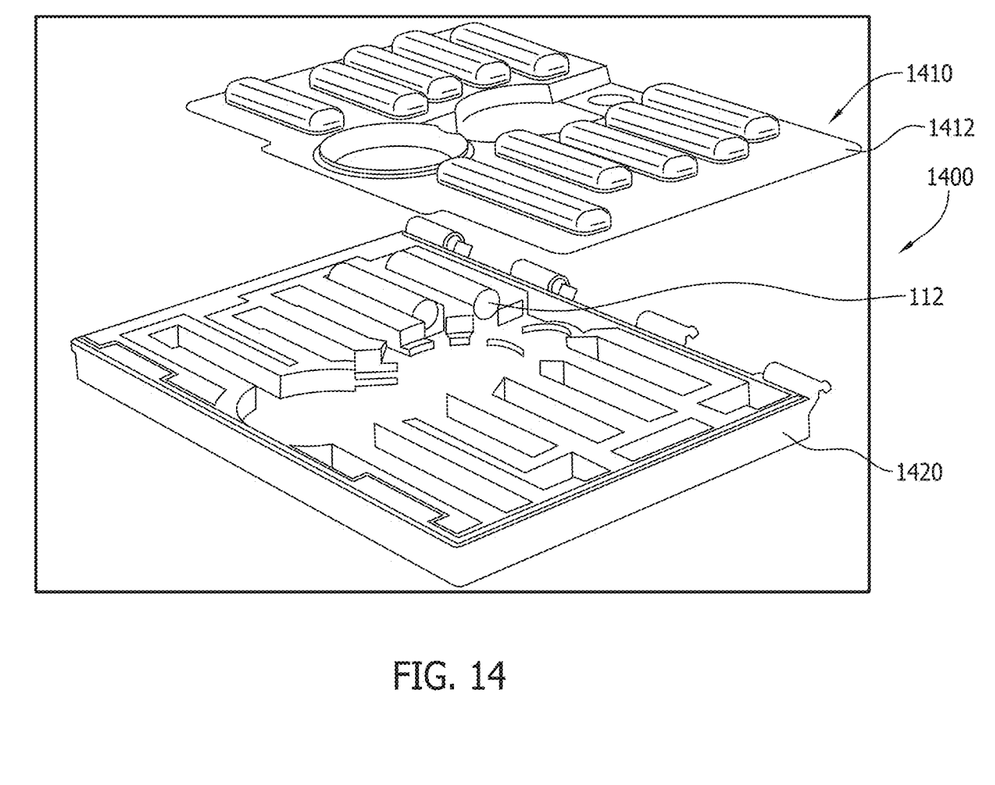
FIG. 14 is a perspective view of an alternative embodiment of a case for a visual indication test kit.
Figure 15:
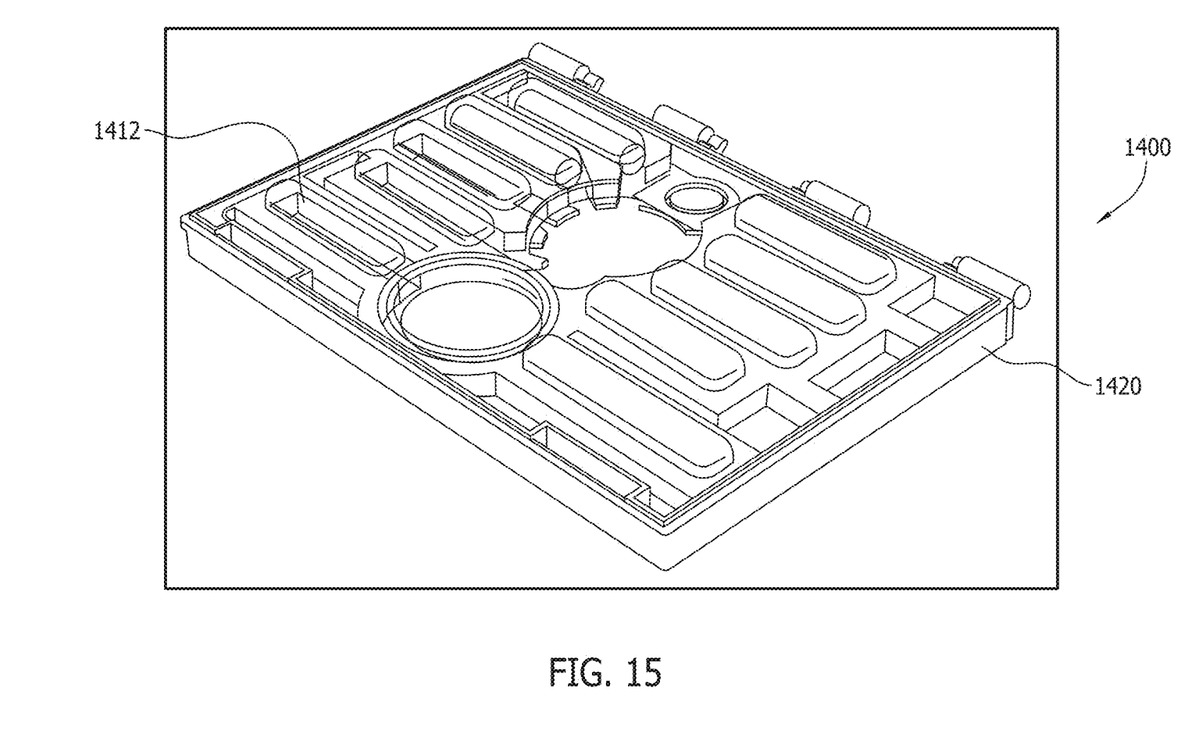
FIG. 15 is a perspective view of the case shown in FIG. 14.

As described above, in some embodiments, the blister pack includes only a thin film top, and does not include a complementary thin film bottom. FIGS. 14 and 15 are perspective views of an alternative embodiment 1400 that includes such a blister pack 1410. As shown in FIGS. 14 and 15, the blister pack 1410 includes a thin film top 1412 that fits over the reagent ampoules 112. For illustration, two reagent ampoules are shown in FIGS. 14 and 15. In FIG. 14, the thin film top 1412 is positioned above and separate from a case bottom 1420, and in FIG. 15, the thin film top 1412 is positioned within and attached to the case bottom 1420.

The systems and methods described herein provide a number of advantages over at least some known visual indication devices. For example, the systems and methods described herein enable conducting multiple visual indication tests from a single extraction by following relatively simple steps, significantly reducing the amount of time needed as compared to at least some known devices that require users to conduct a series of tests, with each test including unique steps. Further, the systems and methods described herein enable users to clearly identify the presence or absence of predetermined chemicals, without requiring users to conduct serial analyses and to interpret results. Moreover, by enabling a user to conduct multiple tests using a single kit, the systems and methods described herein are less expensive than at least some known devices. Further, as all reagents are contained inside of the kit, the systems and methods described herein facilitate minimizing the likelihood that a user will come into contact with the reagents. Finally, during a testing procedure, the user does not contact the plugs in the collector, minimizing contamination from user contact.

Example embodiments of visual indication test kits are described above in detail. The visual indication test kits are not limited to the specific embodiments described herein, but rather, components of the systems and methods described herein may be utilized independently and separately from other components described herein.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A test kit comprising:
   a case comprising:
      a top comprising a plurality of indicator pads and a crushing plate rotatable between a first position and a second position, said crushing plate comprising plurality of crushing ribs;
      a bottom hingedly coupled to said top for positioning said case in an open or closed position, said bottom comprising a plurality of reagent ampoules storing reagents, wherein when said case is positioned in the closed position with said crushing plate in the second position, said plurality of crushing ribs align with and contact said plurality of reagent ampoules to crush said plurality of reagent ampoules to release the reagents stored therein; and
   a collector comprising:
      a collector body comprising a first side and an opposite second side;
      a plurality of swabs extending through said collector body from said first side to said second side, each swab of said plurality of swabs being exposed at said second side of said collector body;
      a removable cover covering said first side of said collector body; and
      a collector handle comprising a first and a second end, wherein said collector handle first end is coupled to said collector body, and wherein said collector is nestable within said case.

2. A test kit in accordance with claim 1, wherein said collector handle is pivotably coupled to said collector body.

3. A test kit in accordance with claim 1, wherein said removable cover is configured to shield said plurality of swabs at said first side of said collector body.

4. A test kit in accordance with claim 1, wherein said bottom further comprises
   at least one wetting agent container storing a wetting agent.

5. A test kit in accordance with claim 4, wherein said at least one wetting agent container is an ampoule.

6. A test kit in accordance with claim 4, wherein said bottom further comprises wetting wicks proximate said at least one wetting agent container, said wetting wicks contacting said plurality of swabs when said collector is nested in said case.

7. A test kit in accordance with claim 1, wherein said bottom further comprises a plurality of reagent wicks proximate said plurality of reagent ampoules, at least one of said plurality of reagent wicks comprising a flow control material configured to control a flow rate of a reagent therethrough.

8. A test kit in accordance with claim 1, wherein at least one of said plurality of swabs comprises a flow control material configured to control flow rate therethrough.

9. A test kit in accordance with claim 1, wherein said collector is insertable into said top such that said plurality of indicator pads align with said plurality of swabs.

10. A test kit in accordance with claim 1, wherein said collector is insertable into said top such that said plurality of swabs are aligned with said plurality of indicator pads in said case.

11. A test kit in accordance with claim 1, wherein a first set of said plurality of swabs are hydrophobic and a second set of said plurality of swabs are hydrophilic.

12. A method for testing substances using a test kit that includes a case including a top hingedly coupled to a bottom, and a collector nested in the case, said method comprising:
   removing the collector from the case, the collector including a collector body that includes a first side and an opposite second side, the collector further including a plurality of swabs extending through the collector body from the first side to the second side, each swab of the plurality of swabs being exposed at the second side of the collector body;
   collecting the substances from a substrate using the plurality of swabs disposed on the collector;
   inserting the collector into the top of the case;
   rotating a crushing plate on the top of the case from a first position to a second position, the crushing plate including a plurality of crushing ribs;
   closing the case such that the plurality of crushing ribs align with and contact a plurality of reagent ampoules in the bottom of the case to crush the plurality of reagent ampoules and release reagents stored therein;
   causing the reagents to mix with the substances collected by the plurality of swabs;
   causing the mixtures to flow to a plurality of indicator pads in the top of the case; and
   viewing the plurality of indicator pads to determine the presence of at least one chemical in the substances.

13. A method in accordance with claim 12, further comprising:
  providing at least one wetting agent to a wetting wick located in the bottom of the case; and
  wetting at least one of the plurality of swabs on the collector by contacting the wetting wick with the at least one swab.

14. A method in accordance with claim 13, wherein providing at least one wetting agent comprises crushing at least one wetting agent ampoule such that the at least one wetting agent flows onto the wetting wick.

15. A method in accordance with claim 12, wherein collecting the substances comprises at least one of dabbing and swabbing a surface with the collector.

16. A method in accordance with claim 12, further comprising inserting the collector into the case such that the plurality of swabs contact the plurality of indicator pads.

\* \* \* \* \*